(12) United States Patent
Lim

(10) Patent No.: US 9,326,595 B2
(45) Date of Patent: May 3, 2016

(54) TWEEZER-APPLICATOR

(75) Inventor: Cindy Sean Yuei Lim, Santa Monica, CA (US)

(73) Assignee: HCT Asia Ltd., Central (HK)

(*) Notice: Subject to any disclaimer, the term of this patent is extended or adjusted under 35 U.S.C. 154(b) by 89 days.

(21) Appl. No.: 13/367,046

(22) Filed: Feb. 6, 2012

(65) Prior Publication Data
US 2013/0199556 A1  Aug. 8, 2013

(51) Int. Cl.
*A46B 15/00* (2006.01)
*B25B 9/02* (2006.01)
*A61B 18/14* (2006.01)
*A46B 9/00* (2006.01)
*A46B 9/02* (2006.01)

(52) U.S. Cl.
CPC .............. *A46B 15/0055* (2013.01); *B25B 9/02* (2013.01); *A46B 9/005* (2013.01); *A46B 9/028* (2013.01)

(58) Field of Classification Search
CPC ................. A45D 26/0066; A61B 2018/1462; A46B 15/0055; B25B 9/02
USPC ........... 606/133, 210, 211; 294/99.2; D28/55
See application file for complete search history.

(56) References Cited

U.S. PATENT DOCUMENTS

| | | | |
|---|---|---|---|
| 4,471,507 A * | 9/1984 | Schwartz | 15/176.6 |
| 4,938,214 A * | 7/1990 | Specht et al. | 606/174 |
| D627,104 S * | 11/2010 | Cho | D24/143 |
| 8,074,666 B2 | 12/2011 | Piao | |
| 2006/0123955 A1* | 6/2006 | Cho | 81/177.2 |
| 2008/0243179 A1* | 10/2008 | Ziv | 606/211 |
| 2009/0131977 A1* | 5/2009 | Ross | 606/211 |
| 2010/0017990 A1* | 1/2010 | Piao | A46B 7/04 15/176.6 |
| 2012/0294666 A1 | 11/2012 | Jang | |
| 2013/0061867 A1* | 3/2013 | Kim et al. | 132/293 |

FOREIGN PATENT DOCUMENTS

AU    2010100143 A4 *  3/2010
WO    WO 2011149210 A2 * 12/2011

OTHER PUBLICATIONS la-tweez Tweezer with Light and Brush; retrieved from: http://www.alibaba.com/product-free/100023364/Light_And_Brush_Tweezer_Tweezers.html retrieved on Jan. 6, 2012; 2 pages.
La-Tweeze Brush with tweezer ; http://www.alibaba.com/product-free/100023370/Brush_With_Tweezer.html retrieved on Jan. 6, 2012; 2 pages.

* cited by examiner

*Primary Examiner* — Katherine M Shi
*Assistant Examiner* — Michael Mendoza
(74) *Attorney, Agent, or Firm* — Seager, Tufte & Wickhem LLP

(57) ABSTRACT

Tweezer-applicators having an applicator arranged linearly with tweezers are disclosed. The applicator may comprise a substantially flat rectangular shaped group of bristles that are arranged substantially straight along a linear axis of the tweezer-applicator. By virtue of having an applicator arranged substantially straight along the linear axis and in line with the tweezers, a user may grip the tweezers without the applicator interfering with a grip of a user and provide the user with precision while applying product to a portion of a body.

19 Claims, 5 Drawing Sheets

TWEEZER-APPLICATOR

BACKGROUND

Tweezers having a brush attached exist for cosmetic purposes. For example, tweezer brushes exist that have a pinching tip and a brush for grooming a user's eyebrows. The pinching tip may be used to remove hair from a body while the brush may be used to apply product to the body.

Generally, tweezers have a pair of levers connected at one end (i.e., at a fulcrum), with the pinching tip at the other end. Existing tweezer brushes have brushes orientated 90 degrees relative to the tweezers, while other existing tweezer brushes have brushes that are orientated about 45 degrees relative to the tweezers. For example, existing tweezer brushes may have a group of bristles fixed at the fulcrum of the tweezers and have a 45 or 90 degree angle, relative to the pair of levers.

While these tweezer brushes may groom a user's body, they do not provide a high level of precision while applying a product to a body. Accordingly, there remains a need in the art for improved cosmetic tweezer brushes that provide a high level of precision while applying product to a user's body.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Overview

Figure 1:
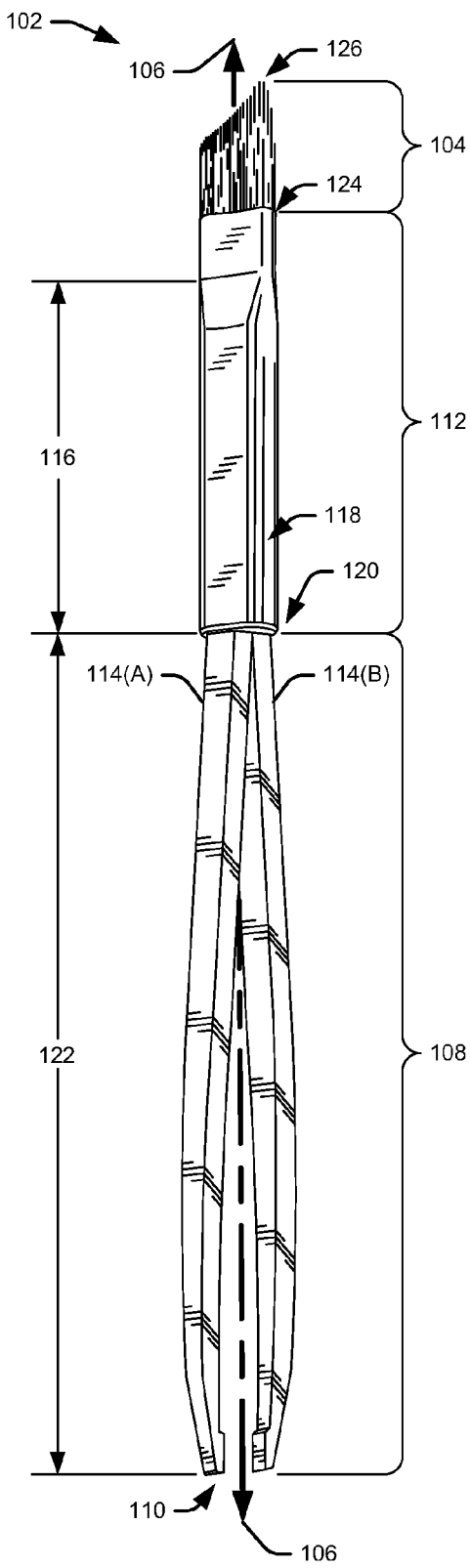
FIG. 1 depicts a perspective view of an illustrative tweezer-applicator having an applicator coupled to tweezers by a ferrule, the applicator and tweezers being arranged substantially aligned along a linear axis of the tweezer-applicator.

This application describes tweezer-applicators having an applicator for applying a cosmetic product to a surface, the applicator being integrated and aligned linearly with tweezers. By virtue of having a tweezer-applicator having an applicator arranged linearly with the tweezers, tweezer-applicators according to this disclosure are adaptable to provide a user with more precision while applying product to a portion of a body than existing tweezer-applicators having an applicator arranged 45 degrees or 90 degrees relative to the tweezers. In addition to providing precise application of product to a body, by virtue of having an applicator arranged linearly with the tweezers, tweezer-applicators according to this disclosure are adaptable to provide an improved gripping area. For example, because the applicator is arranged linearly with the tweezers, the applicator does not interfere with a hand of a user when the user grips the tweezers. Consequently, the user is not likely to bend or damage the applicator inadvertently. Additionally, with the applicator axially aligned with the tweezers, the user is less likely to get cosmetic product from the applicator on her hand while using the tweezers.

In one example, the tweezer-applicator may comprise a pinching tip (i.e., the jaws of the tweezer) opposite to a ferrule and an applicator fixed to the ferrule, where a plan extending through a center of the pinching tip (i.e., between the jaws of the tweezers), the ferrule, and the applicator form a substantially straight line.

In another example, the tweezer-applicator may not include a separate ferrule. In that case, the ferrule may be formed integrally with a handle or fulcrum of the tweezer and the applicator may be retained by a portion of the handle or fulcrum of the tweezer. This may be accomplished by a pocket or cavity formed in the handle or fulcrum of the tweezer into which the applicator may be installed and retained (e.g., by adhesive, thermal bonding, crimping, interference fit, snap fit, magnetic retention, or the like). In one specific example, the applicator may be magnetically and removably coupled to the handle of the tweezer. In that case, the handle may comprise a ferrous or other magnetic material that is attractable by a magnet in the applicator and/or the handle may include a magnet and the applicator may include a ferrous or other magnetic material that is attractable by a magnet in the handle of the tweezer.

The pinching tip may comprise a first planar surface facing a second planar surface, the first planar surface being parallel to the second planar surface defining a plane of reflection equal distant between the first and second planar surfaces. In other words, the plan of reflection bisects the tweezers. In another example, in which the pinching tip comprises first and second planar surface that are parallel, the applicator may include a group of bristles defining a substantially flat rectangular shape extending away from the handle of the tweezer and substantially coplanar with the plane of reflection.

In various embodiments including a ferrule, the tweezer-applicator described herein may comprise lever arms connected to each other at an interior of a ferrule. In another example, each of the lever arms may be individually fixed in an interior of the ferrule.

While the tweezer-applicators are described in various embodiments herein in the context of tweezer-applicators for cosmetic grooming, the tweezer-applicators may also be used and adapted for other purposes. For example, the tweezer-applicators may be used and adapted for use in the medical environment, manufacturing environment, auto body repair environment, or the like.

While the applicators are described in various embodiments herein as having a substantially flat rectangular shape, the applicators may be other shapes. For example, the applicator may be substantially cylindrical, conical, oval, flat-triangular, or the like.

Illustrative Tweezer-Applicators

FIG. 1 depicts a perspective view of an illustrative tweezer-applicator 102 having an applicator 104 arranged substantially straight along a linear axis 106, such that the applicator 104 is substantially parallel and directly in line with tweezers 108, which are arranged with a centroid of tweezers substantially straight along the same linear axis 106. Because the applicator 104 is arranged substantially straight along the linear axis 106 and in line with the tweezers 108, a user may grip the tweezers 108 without the applicator 104 interfering with the hand gripping the tweezers 108. Further, because the applicator 104 is arranged substantially straight along the linear axis 106 and in line with the tweezers 108, a user may wield the applicator 104 with precision. For example, because the applicator 104 and the tweezers 108 are in line with each other, a user may grip the tweezers 108 and apply product to a portion of the body at a generally perpendicular orientation (i.e., much like holding a writing utensil). For example, a user may grip the tweezers 108 and apply product to the eyebrows where the linear axis 106 of the tweezer-applicator 102 is at a generally perpendicular orientation to the user's face rather than at a generally horizontal orientation to the user's face. The generally perpendicular orientation may range from at least about 30 degrees to at most about 120 degrees relative to a users face, which provides for accurate application of product to a user's eyebrows. For example, a user may wield the tweezer-applicator 102 at a generally perpendicular orientation to fill and extend the eyebrows by following the arch of the eyebrow with small, feather-like strokes.

The tweezers 108 may include a pinching tip 110 opposite to a ferrule 112, and a pair of lever arms 114(A) and 114(B) extending from the pinching tip 110 to the ferrule 112. The ferrule 112 and/or the lever arms 114(A) and 114(B) may be formed of metal, plastic, composite, or wood. In one specific example, the ferrule 112 and the lever arms 114(A) and 114 (B) may be formed of spring steel.

While the pair of lever arms 114(A) and 114(B) are illustrated as extending to the ferrule 112, the pair of lever arms 114(A) and 114(B) may extend a distance 116 into an interior 118 of the ferrule 112. The distance 116 may be at least about 0.5 inch (13 millimeters) and up to at most about 3 inches (76 millimeters). The pair of lever arms 114(A) and 114(B) may be connected to each other in the interior 118 of the ferrule 112, forming a fulcrum 120 for the lever arms 114(A) and 114(B). For example, the lever arms 114(A) and 114(B) may be connected to each other via a weld and extend the distance 116 into the interior 118 of the ferrule. Alternatively, the lever arms 114(A) and 114(B) may be formed of a single unit of material connected to each other via a bend as a result of folding the single unit of material together and extend the distance 116 into the interior 118 of the ferrule.

The pair of lever arms 114(A) and 114(B) may or may not be connected to each other in the interior 118 of the ferrule 112. For example, each of the lever arms 114(A) and 114(B) may be individually fixed to the ferrule 112 in the interior 118 of the ferrule 112. For example, the pair of lever arms 114(A) and 114(B) may be fixed in the interior 118 of the ferrule 112 via a compression fit, a press fit, or a snap fit. For example, the ferrule 112 may provide sufficient force on the lever arms 114(A) and 114(B) to compress the pair of lever arms 114(A) and 114(B) together, forming the fulcrum 120. Additionally or alternatively, the pair of lever arms 114(A) and 114(B) may be fixed in the interior 118 of the ferrule 112 via an adhesive or a fastener, forming the fulcrum 120.

The pinching tip 110 may be separated a distance 122 from the ferrule 112. The distance 122 may be at least about 2 inches (51 millimeters) and up to at most about 7 inches (178 millimeters). While the pinching tip 110 of the tweezers 108 is illustrated as having a flat angled pinching tip 110, the pinching tip 110 may be any other shape. For example, the pinching tip 110 may have a flat broad pinching tip, a flat blunt angled pinching tip, a flat broad angled pinching tip, a flat square pinching tip, a flat round pinching tip, a flat bent broad pinching tip, a blunt round pinching tip, a long needle pinching tip, a pointed pinching tip, or any other conventional tweezer pinching tip.

The applicator 104 may include a first end 124 fixed to the ferrule 112 and a second end 126 distal to the first end 124 for applying product to a body. While the second end 126 is illustrated as having a triangular shaped surface for applying product to a body, the second end 126 may be any other shape for applying product to a body. For example, the second end 126 may have a square shaped surface, a convex shaped surface, a cone shaped surface, or the like for applying product to a body. By way of example and not limitation, several alternative applicator shapes are shown in FIGS. 4A-4D. Further, while the applicator 104 is illustrated as being a group of bristles, the applicator 104 may additionally or alternatively comprise a sponge, a flocking, a comb, a combination of any of the foregoing, or the like.

Figure 2A:
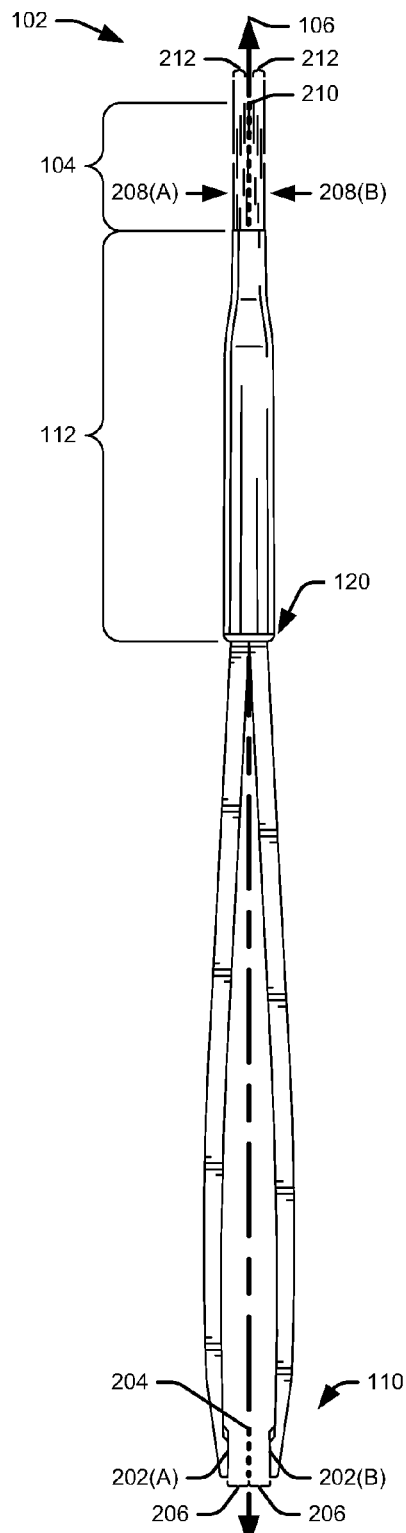
FIG. 2A and FIG. 2B depict a side view and a front view, respectively, of the tweezer-applicator illustrated in FIG. 1.
Figure 2B:
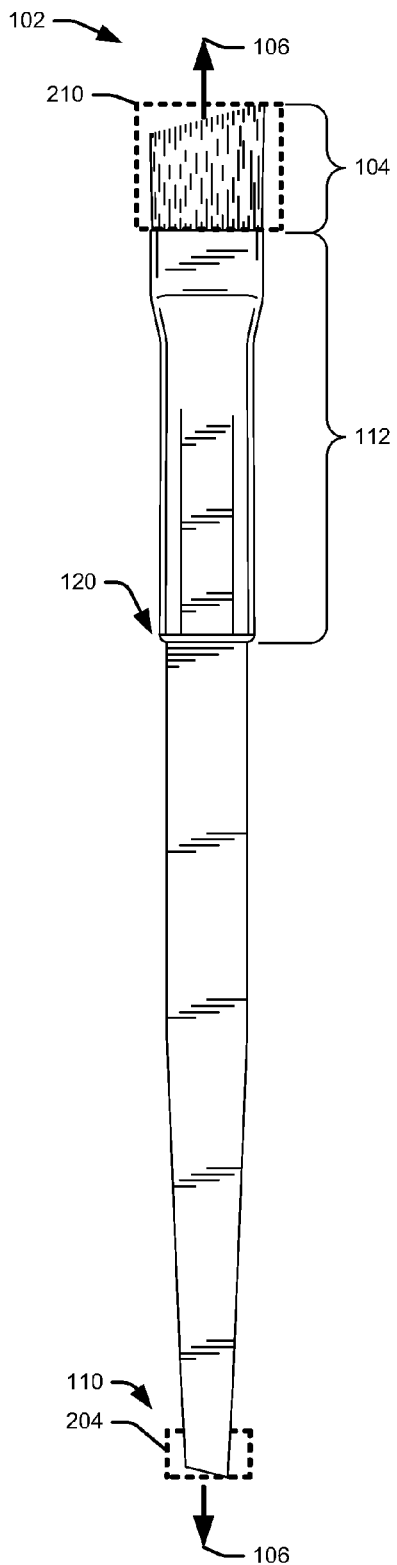

FIG. 2A and FIG. 2B depict a side view and a front view, respectively, of the tweezer-applicator 102 illustrated in FIG. 1. FIGS. 2A and 2B illustrate the pinching tip 110 of the tweezer-applicator 102 may comprise a first planar surface 202(A) facing a second planar surface 202(B). The first planar surface 202(A) may be parallel to the second planar surface 202(B) and define a plane of symmetry 204 (extending into and out of the page). The plane of symmetry 204 being equal distant 206 between the first and second planar surfaces 202 (A) and 202(B) such that the linear axis 106 lies in the plane of symmetry 204.

FIGS. 2A and 2B illustrate the applicator 104 as being a substantially flat rectangular shaped group of bristles extending away from the ferrule 112. The substantially flat rectangular shaped group of bristles may be formed of natural fibers (e.g., animal hair) or synthetic fibers (e.g., plastic or rubber), or the like. The applicator 104 may comprise a group of bristles having a first planar surface 208(A) opposite a second planar surface 208(B). The first planar surface 208(A) may be parallel to the second planar surface 208(B) about a plane of symmetry 210. The plane of symmetry 210 being equal distant 212 between the first and second planar surfaces 208(A) and 208(B) and aligned with the linear axis 106. The applicator 104 comprising the substantially flat rectangular shaped group of bristles may be arranged such that the plane of symmetry 210 is substantially coplanar with the pane of symmetry 204 as shown in FIG. 2A. Alternatively, the plane or symmetry 210 may intersect the plane of symmetry 204 at an oblique angle. For example, the plane of symmetry 210 of the applicator 104 may be arranged 90 degrees, 45 degrees, 30 degrees, 15 degrees, etc., relative to the plane of symmetry 204 of the pinching tip 110.

Figure 3A:
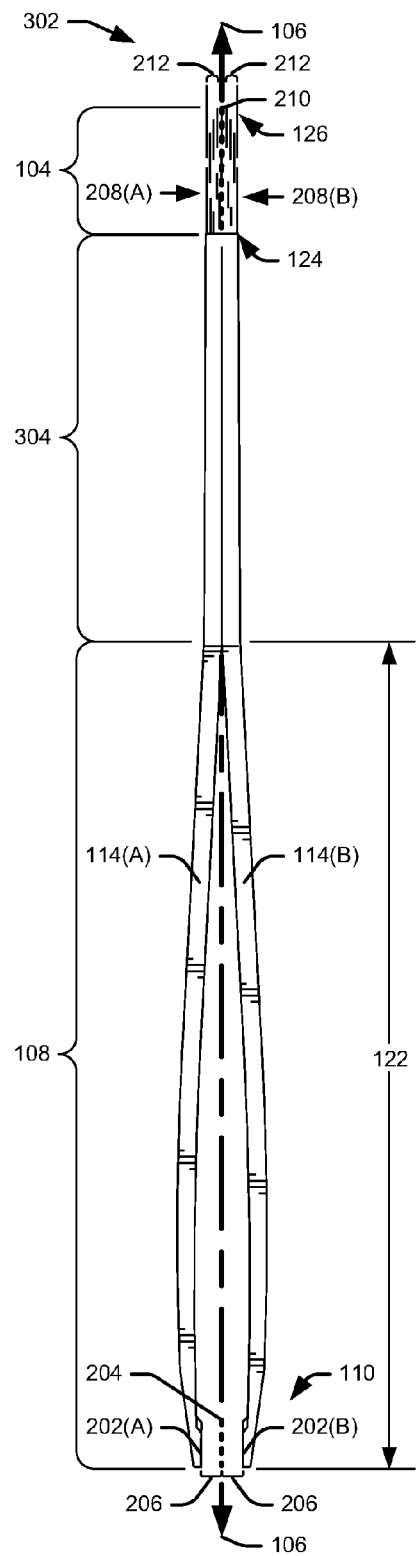
FIG. 3A and FIG. 3B depict a side view and a front view, respectively, of an illustrative tweezer-applicator without a ferrule.
Figure 3B:
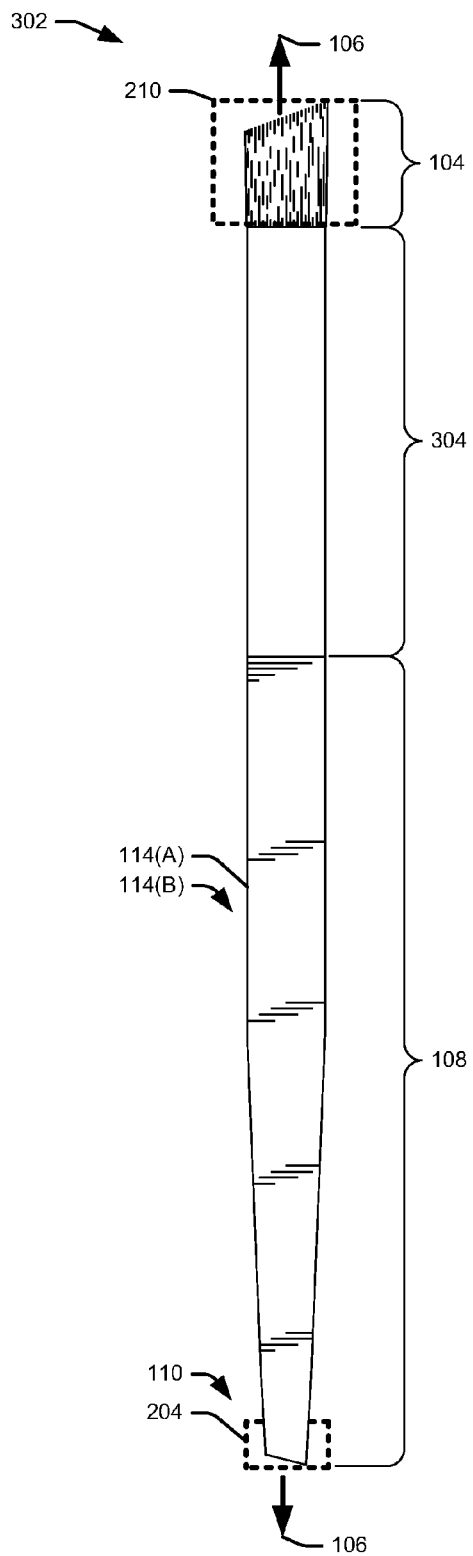

FIG. 3A and FIG. 3B depict a side view and a front view, respectively, of a tweezer-applicator 302. Tweezer-applicator 302 may include many similar features as tweezer-applicator 102, except the tweezer-applicator 302 does not include a ferrule (e.g., ferrule 112). For example, tweezer-applicator 302 may include a ferrule formed integrally with a handle or fulcrum of the tweezer 108. For example, a cavity may be formed in the handle or fulcrum 304 of the tweezer 108 into which the applicator 104 may be installed and retained (e.g., by adhesive, thermal bonding, crimping, interference fit, snap fit, magnetic retention, or the like). In one specific example, the applicator 104 may be magnetically and removably coupled to the handle or fulcrum 304 of the tweezer 108. In another specific example, the applicator 104 may be rotatably coupled to the handle of the tweezer 108. In that case, the handle may comprise a pivot rotatably coupling the applicator 104 to the handle or fulcrum 304 of the tweezer 108. The tweezer-applicator 302 includes the pinching tip 110 opposite to a fulcrum 304 and the pair of lever arms 114(A) and 114(B) extending from the pinching tip 110 to the fulcrum 304. The pinching tip 110 may be separated the distance 122 from the fulcrum 304.

Tweezer-applicator 302 includes the applicator 104 having a first end 124 fixed to the fulcrum 304 and the second end 126 distal to the first end 124 for applying product to a body. The applicator 104 may comprise a group of bristles fixed to the fulcrum 304 and extend away from the fulcrum 304 substantially linearly with the linear axis 106. For example, as discussed above with respect to FIGS. 1, 2A, and 2B, the applicator 104 may be arranged substantially straight along the linear axis 106 such that the applicator 104 is substantially parallel and directly in line with tweezers 108. For example, the pinching tip 110 and the fulcrum 304 of the tweezers 108 and the second end 126 of the applicator 104 form a substantially straight line along the linear axis 106.

Figure 4A:
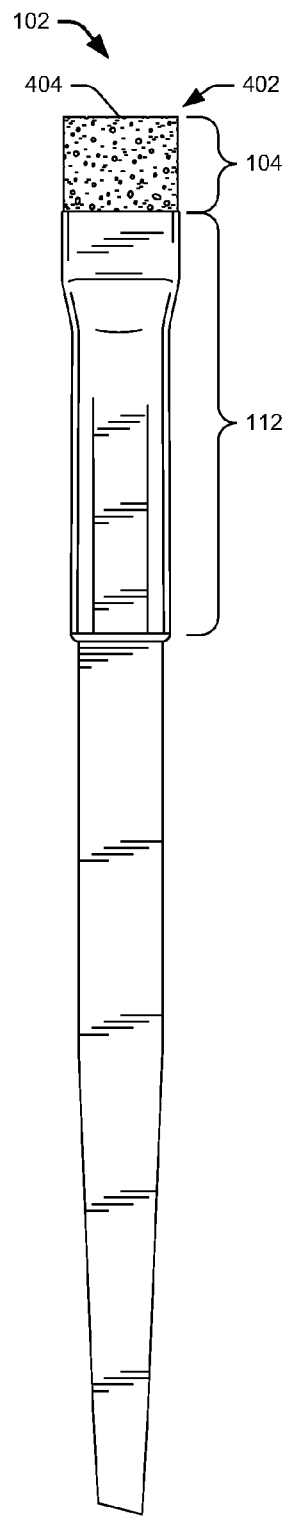
FIGS. 4A, 4B, 4C, and 4D each depict front views of example applicators that may be used with tweezer-applicator of FIG. 1 or FIGS. 3A and 3B, each applicator having a different shape.
Figure 4B:
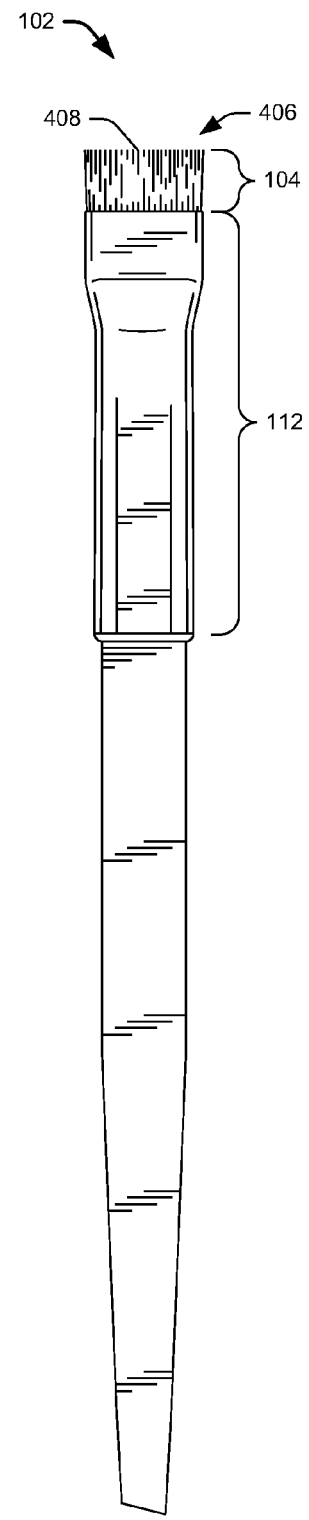
Figure 4C:
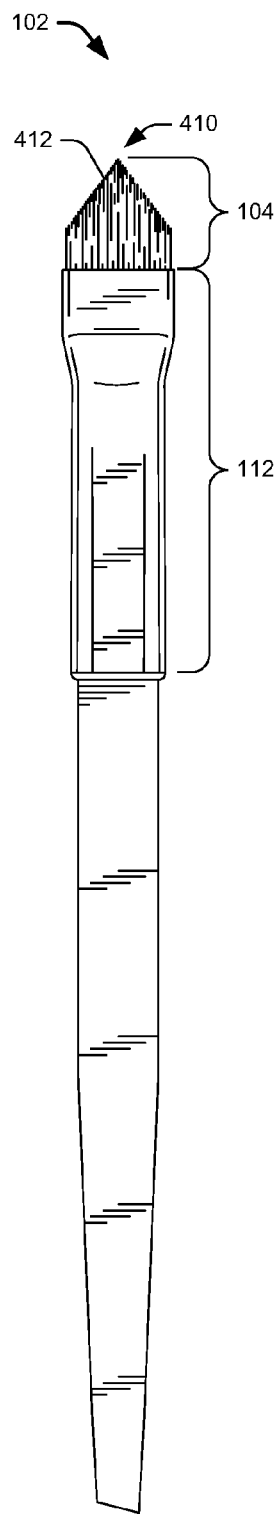
Figure 4D:
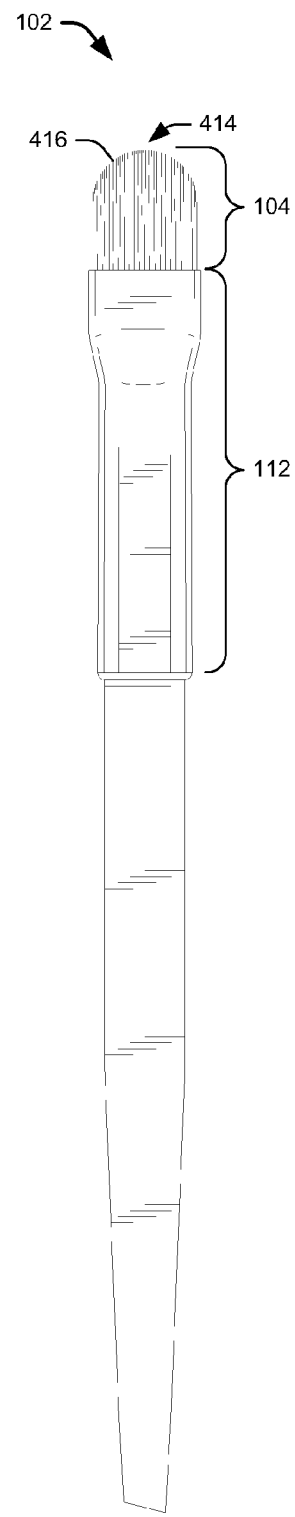

FIGS. 4A, 4B, 4C, and 4D each depict front views of the tweezer-applicator 102 having a different shaped applicator 104. FIG. 4A depicts the applicator 104 may be a substantially flat rectangular shaped sponge 402 extending away from the ferrule 112 having a square shaped application surface 404. FIG. 4B depicts the applicator 104 may be a substantially flat rectangular shape group of bristles 406 extending away from the ferrule 112 having a square shaped application surface 408. FIG. 4C depicts the applicator 104 may be a substantially flat triangular shaped group of bristles 410 extending away from the ferrule 112 having a triangular application surface 412. FIG. 4D depicts the applicator 104 may be a substantially flat convex shaped group of bristles 414 extending away from the ferrule 112 having a convex application surface 416. These alternative applicator configurations are merely illustrative and other suitable applicator shapes may be used depending on the intended use of the tweezer-applicator.

CONCLUSION

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. For example, in various embodiments, any of the structural features and/or methodological acts described herein may be rearranged, modified, or omitted entirely. For example, the shape, size, and configuration of the tweezers, ferrule, and applicator may be varied.

What is claimed is:

1. A tweezer-applicator comprising:
    tweezers having a pinching tip opposite to a fulcrum, and a pair of lever arms extending from the pinching tip to the fulcrum;
    an applicator comprising a group of bristles having a first end fixed to the fulcrum and a second end distal to the first end for applying product to a body;
    a ferrule fixing the first end of the applicator to the fulcrum of the tweezers, wherein the pair of lever arms extend a distance into an interior of the ferrule, and the pinching tip and the fulcrum of the tweezers and the second end of the applicator form a substantially straight line such that the second end of the applicator extends substantially opposite the fulcrum along the straight line; and
    wherein the pinching tip comprises a first planar surface disposed at a first end of the pair lever arms and a second planar surface disposed at a second end of the pair of lever arms, the first planar surface facing the second planar surface, and the first planar surface and the second planar surface being equal distant about a plane of symmetry arranged between the first and second planar surfaces, and the applicator comprises a substantially flat cross-section extending away from the fulcrum parallel and coplanar with the plane of symmetry;
    wherein the applicator is permanently fixed to the fulcrum.

2. The tweezer-applicator according to claim 1, wherein the pinching tip of the tweezers comprises a substantially flat pinching tip.

3. The tweezer-applicator according to claim 1, wherein the second end of applicator for applying product to the body comprises a square, a triangular, or convex shaped profile.

4. The tweezer-applicator according to claim 1, wherein the group of bristles extends substantially parallel to a length of the tweezers.

5. The tweezer-applicator according to claim 1, wherein the applicator extends axially opposite the tweezers.

6. The tweezer-applicator according to claim 1, wherein the applicator comprises a group of bristles having a first planar surface opposite a second planar surface and the first and second planar surfaces are parallel with the plane of symmetry.

7. The tweezer-applicator according to claim 1, wherein the ferrule comprises an interior to receive tweezer arms that:
    compresses the tweezer arms together; or
    encompass the fulcrum of the tweezer arms.

8. A tweezer-applicator comprising:
    tweezers comprising a pinching tip separated a distance from a fulcrum, the pinching tip and the fulcrum being arranged linearly on a linear axis of the tweezers;
    a pair of lever arms extending from the pinching tip to the fulcrum;
    a body fixed to the fulcrum, wherein the pair of lever arms extend a distance into an interior of the body;
    a group of bristles permanently fixed to the body and extending away from the fulcrum substantially linearly with the linear axis of the tweezers; and
    wherein the pinching tip comprises a first planar surface disposed at a first end of the pair lever arms and a second planar surface disposed at a second end of the pair of lever arms, the first planar surface facing the second planar surface, and the first planar surface and the second planar surface being equal distant about a plane of symmetry arranged between the first and second planar surfaces, and the group of bristles comprise a substantially flat cross-section extending away from the fulcrum parallel and coplanar with the plane of symmetry.

9. The tweezer-applicator according to claim 8, wherein the group of bristles is formed of natural fibers or synthetic fibers.

10. The tweezer-applicator according to claim 8, wherein the pair of lever arms extending from the pinching tip to the fulcrum is formed of metal, plastic, composite, and/or wood.

11. A tweezer-applicator comprising:
    a first planar surface arranged at a pinching tip of a lever arm;
    a second planar surface arranged at a pinching tip of another lever arm, wherein the first and second planar surfaces are parallel and define a plane of symmetry arranged equal distant between the first and second planar surfaces;
    a ferrule fixed to the lever arms at ends of the lever arms opposite to the pinching tips, the lever arms disposed a distance in an interior of the ferrule; and
    a group of bristles comprising a substantially flat cross-section permanently fixed to the ferrule and extending away from the ferrule parallel and coplanar with the plane of symmetry of the pinching tips of the lever arms.

12. The tweezer-applicator according to claim 11, wherein the lever arms are connected to each other in the interior of the ferrule, forming a fulcrum for the lever arms.

13. The tweezer-applicator according to claim 12, wherein the lever arms are connected to each other via a weld.

14. The tweezer-applicator according to claim 12, wherein the lever arms are formed of a single unit of material and are connected to each other via a bend.

15. The tweezer-applicator according to claim 11, wherein each lever arm is fixed in the interior of the ferrule via a compression fit.

16. The tweezer-applicator according to claim 11, wherein each lever arm is fixed in the interior of the ferrule via a fastener.

17. The tweezer-applicator according to claim 11, wherein each lever arm is fixed in the interior of the ferrule via an adhesive.

18. The tweezer-applicator according to claim 11, wherein the lever arms are formed of metal, plastic, composite, or wood.

19. The tweezer-applicator according to claim 11, wherein the ferrule is formed of metal, plastic, or composite.

* * * * *